United States Patent
Cuervo et al.

(10) Patent No.: US 11,834,424 B2
(45) Date of Patent: *Dec. 5, 2023

(54) COMPOUNDS USEFUL AS CHAPERONE-MEDIATED AUTOPHAGY MODULATORS

(71) Applicant: ALBERT EINSTEIN COLLEGE OF MEDICINE, Bronx, NY (US)

(72) Inventors: Ana Maria Cuervo, Bronx, NY (US); Evripidis Gavathiotis, Bronx, NY (US)

(73) Assignee: ALBERT EINSTEIN COLLEGE OF MEDICINE, Bronx, NY (US)

( * ) Notice: Subject to any disclaimer, the term of this patent is extended or adjusted under 35 U.S.C. 154(b) by 74 days.

This patent is subject to a terminal disclaimer.

(21) Appl. No.: 17/270,522

(22) PCT Filed: Aug. 30, 2018

(86) PCT No.: PCT/US2018/048821
§ 371 (c)(1),
(2) Date: Feb. 23, 2021

(87) PCT Pub. No.: WO2020/046335
PCT Pub. Date: Mar. 5, 2020

(65) Prior Publication Data
US 2021/0317095 A1    Oct. 14, 2021

(51) Int. Cl.
*C07D 265/36* (2006.01)
*C07D 241/42* (2006.01)

(52) U.S. Cl.
CPC ......... *C07D 265/36* (2013.01); *C07D 241/42* (2013.01)

(58) Field of Classification Search
CPC ........................ C07D 256/36; C07D 241/42
See application file for complete search history.

(56) References Cited

U.S. PATENT DOCUMENTS

| | | | | |
|---|---|---|---|---|
| 8,273,743 B2* | 9/2012 | Koehler | ............... | C07D 401/14 |
| | | | | 514/249 |
| 9,512,092 B2* | 12/2016 | Cuervo | ............... | C07C 279/22 |
| 9,890,143 B2* | 2/2018 | Cuervo | ............... | C07D 413/10 |
| 10,189,827 B2 | 1/2019 | Cuervo et al. | | |
| 10,766,886 B2* | 9/2020 | Cuervo | ............... | C07C 279/22 |
| 2013/0035304 A1 | 2/2013 | Walensky et al. | | |
| 2015/0166492 A1* | 6/2015 | Cuervo | ............... | C07C 279/22 |
| | | | | 435/7.8 |
| 2018/0141937 A1* | 5/2018 | Cuervo | ............... | C07C 279/22 |

FOREIGN PATENT DOCUMENTS

| | | |
|---|---|---|
| JP | 2013-518816 A | 5/2013 |
| WO | 2006078283 A2 | 7/2006 |
| WO | 2016111957 A1 | 7/2016 |

OTHER PUBLICATIONS

Supplementary European Search Report for EP Application No. 18931720.9-1110; dated Apr. 22, 2022; 11 pages.
Zhang et al., "Cystinosin, the Small GTPase Rab11, and the Rab7 Effector RILP Regulate Intracellular Trafficking of the Chaperone-Mediated Autophagy Receptor LAMP2A," Journal of Biological Chemistry, (2017), vol. 292, (No. 25), 10328-10346.
International Search Report; International Application No. PCT/US2018/048821; International Filing Date—Aug. 30, 2018; dated Oct. 18, 2018; 7 pages.
Written Opinion; International Application No. PCT/US2018/048821; International Filing Date—Aug. 30, 2018; dated Oct. 18, 2018; 7 pages.
Sabegh et al., "The Regioselective Catalyst-Free Synthesis of Bis-Quinoxalines and Bis-Pyrido[2,3-b]Pyrazines by Double Condensation of 1,4-Phenylene-Bis-Glyoxal with 1,2-Diamines," Heterocyclic Communications, (2018), vol. 24, (No. 4), 193-196.
Extended European Search Report for European Application No. 23157560.6, dated Jun. 20, 2023, 9 pages.

* cited by examiner

*Primary Examiner* — D Margaret M Seaman
(74) *Attorney, Agent, or Firm* — CANTOR COLBURN LLP

(57) ABSTRACT

Compounds and pharmaceutically acceptable salts thereof of Formula I are disclosed. Certain compounds and salts of Formula I are active as CMA modulators. The disclosure provides pharmaceutical compositions containing a compound of Formula I.

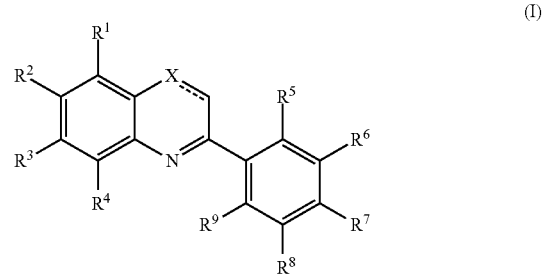

19 Claims, 4 Drawing Sheets

COMPOUNDS USEFUL AS CHAPERONE-MEDIATED AUTOPHAGY MODULATORS

STATEMENT OF GOVERNMENT INTEREST

The National Institutes of Health funded the subject matter of this disclosure. The United States Government has certain rights in this application.

CROSS REFERENCE TO RELATED APPLICATIONS

This application is a National Stage application of and claims priority to PCT/2018/048821, filed Aug. 30, 2018, which is hereby incorporated by reference in its entirety.

FIELD OF THE DISCLOSURE

The present disclosure relates to 3-phenyl-benzoxazines and 3-phenyl-quinoxazolines as CMA modulators and pharmaceutical compositions containing these compounds.

BACKGROUND

Autophagy is a process by which unnecessary or dysfunctional proteins present in the cytosol are degraded in lysosomal lumen. In chaperone-mediated autophagy (CMA), proteins are individually selected and targeted from the cytosol to the lysosomal lumen by directly crossing the membrane. CMA plays a role in cellular quality control by facilitating the removal of damaged or abnormal proteins and surplus subunits of multi-protein complexes. CMA, when activated, functions: to break down proteins to provide amino acids for fuel during prolonged periods of starvation; to remove oxidized proteins during oxidative stress; and to remove damaged proteins after toxic chemical exposure. CMA also has regulatory functions in the cell as it can modulate the activity of other cellular processes (i.e. glycolysis, lipogenesis, lipolysis, cell cycle, DNA repair, etc.) through degradation of key proteins that participate in each of these processes.

CMA is a multiple step process. The chaperone, heat shock cognate protein 70 (Hsc70), recognizes and binds a pentapeptide motif (e.g., KFERQ) of the protein substrate to be degraded. Once bound to Hsc70, the protein substrate is targeted to the surface of the lysosome where it interacts with the cytosolic tail of the monomeric form of the membrane-bound lysosome-associated membrane protein type 2A (LAMP-2A) receptor. Upon binding of the Hsc70-protein substrate complex to the LAMP-2 receptor, this triggers LAMP-2A to form a multimeric complex ("translocation complex") with the associated lysosomal proteins. It is only after the formation of the translocation complex that the protein substrate can cross the membrane from the cytosol to the lysosome. Once the substrate is translocated into the lysosomal lumen, LAMP-2A breaks away from the translocation complex and the protein substrate undergoes degradation.

Both diminished and enhanced CMA activity have been associated with human disease. In particular, problems in the functioning of the translocation complex contribute to the development of disease pathologies. For example, reduced CMA activity is associated with: neurodegenerative diseases, such as tauopathies (Frontotemporal Dementia, Alzheimer's disease), Parkinson's Disease, Huntington's Disease, prion diseases, amyotrophic lateral sclerosis, retinal and macular degeneration, leber congenital amaurosis, diabetes, acute liver failure, NASH, hepatosteatosis, alcoholic fatty liver, renal failure and chronic kidney disease, emphysema, sporadic inclusion body myositis, spinal cord injury, traumatic brain injury, lysosomal storage disorders, including but not limited to cystinosis, galactosialydosis, mucopolisacaridosis, a cardiovascular disease, or immunosenescence. Alternatively, upregulation of CMA activity is linked to the survival and proliferation of cancer cells and also occurs in Lupus, for example. However, known small molecules that modulate CMA are non-specific and affect the activity of other cellular quality control mechanisms. Therefore, there is a need for compounds that modulate CMA activity for the treatment of diseases and conditions associated with the increased or decreased CMA activity.

SUMMARY

The inventors have discovered a class of compounds and salts of Formula I that modulate CMA. Some compounds activate an RAR receptor. Some compounds inactivate an RAR receptor.

Retinoic acid receptors (RARs) are nuclear hormone receptors that act as transcription factors, regulating cell division, cell growth and cell death. There are three types of RARs identified in mammals (RARα, RARβ, and RARγ) coded by different genes. The expression of RARβ and RARγ is tissue-dependent, whereas RARα is ubiquitously expressed. The natural ligands of RARs are all-trans retinoic acid (ATRA) and 9-cis retinoic acid (9-cis RA).

RARα signaling inhibits LAMP-2A transcription and the expression of other CMA genes. When RARα is activated upon binding of RARα agonists (e.g. ATRA, 9-cis RA or derivatives thereof), transcription of LAMP-2A decreases and there is less LAMP-2A receptor present to participate in CMA. Alternatively, an antagonist binding to RARα would potentially block the inhibition of the transcription of LAMP-2A, resulting in more LAMP-2A receptor present to participate in CMA.

The disclosure includes compounds and salts of Formula I

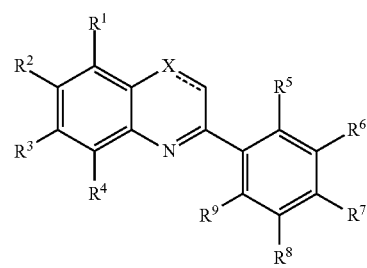

or a pharmaceutically acceptable salt thereof, wherein
X is O and ====== is a single bond, or X is N and ====== is an aromatic bond;
$R^1$, $R^3$, and $R^4$ are independently chosen from hydrogen, halogen, hydroxyl, $C_1$-$C_6$alkyl, and $C_1$-$C_6$alkoxy;
$R^2$ is halogen;
$R^5$, $R^6$, $R^8$, and $R^9$ are independently chosen from hydrogen, halogen, hydroxyl, $C_1$-$C_6$alkyl, and $C_1$-$C_6$alkoxy;
$R^7$ is —$NR^{10}COR^{11}$ or —$NR^{10}SO_2R^{11}$, or
$R^7$ is phenyl, napthyl, and mono- or bi-cyclic heteroaryl each of which is optionally substituted with halogen, hydroxyl, cyano, —CHO, —COOH, amino, and $C_1$-$C_6$alkyl in which any carbon-carbon single bond is optionally replaced by a carbon-carbon double or triple bond, any methylene group is optionally replaced by O, S, or $NR^{12}$, and optionally substituted with one or more substituents independently chosen from halogen, hydroxyl, cyano, amino, and oxo; and one substituent chosen from —$NR^{10}COR^{11}$ and $NR^{10}SO_2R^{11}$;

$R^{10}$ is independently chosen at each occurrence from hydrogen and $C_1$-$C_6$alkyl;

$R^{11}$ is independently chosen at each occurrence from hydrogen, $C_1$-$C_6$alkyl, $C_1$-$C_2$haloalkyl, monocyclic aryl and heteroaryl, each of which monocyclic aryl and heteroaryl is optionally substituted with one or more substituents independently chosen from halogen, hydroxyl, cyano, $C_1$-$C_6$alkyl, $C_1$-$C_6$alkoxy, $C_1$-$C_2$haloalkyl, and $C_1$-$C_2$haloalkoxy; and $R^{12}$ is hydrogen, $C_1$-$C_6$alkyl, or ($C_3$-$C_7$cycloalkyl)$C_0$-$C_2$alkyl.

Pharmaceutical compositions comprising a compound or salt of Formula I together with a pharmaceutically acceptable carrier are disclosed.

The disclosure provides pharmaceutical compositions comprising a compound of Formula I, or a pharmaceutically acceptable salt of Formula I, together with a pharmaceutically acceptable carrier.

The disclosure further provides a method of selectively activating chaperone-mediated autophagy in a subject in need thereof by administering a therapeutically effective amount of a compound of Formula I, or salt thereof, to the subject. The disclosure provides the use of a compound of Formula I, or salt thereof, for activation of chaperone-mediated autophagy in a subject in need thereof.

BRIEF DESCRIPTION OF THE DRAWINGS

FIGS. 1A-1C: FIG. 1A shows the effect of CA39 and CA39.1 (CA3901) on CMA; FIG. 1B shows the effect of CA77 and CA77.1 (CA7701) on CMA FIG. 2A shows the concentrations of CA77.1 in ICR (CD-1) mouse plasma after i.v. and p.o. administration of a 10 mg/kg dose; FIG. 2B shows the concentrations of CA77.1 in ICR (CD-1) mouse brain after i.v. and p.o. administration of a 10 mg/kg dose.

FIG. 3A shows CMA activation dose dependence in cells 12 h post-administration of CA39, CA77, or CA77.1; FIG. 3B shows CMA activation dose dependence in cells 24 h post-administration of CA39, C A77, or CA77.1.

DETAILED DESCRIPTION

Chemical Description and Terminology

Figure 1A:
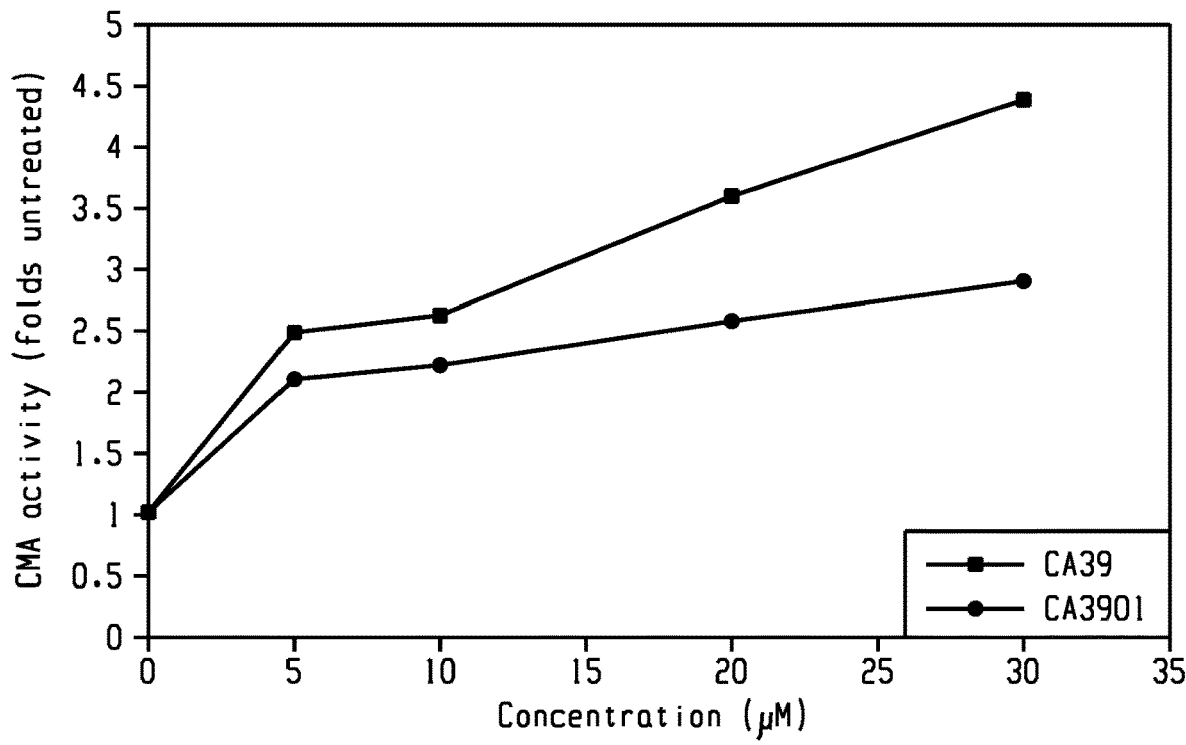
Figure 1B:
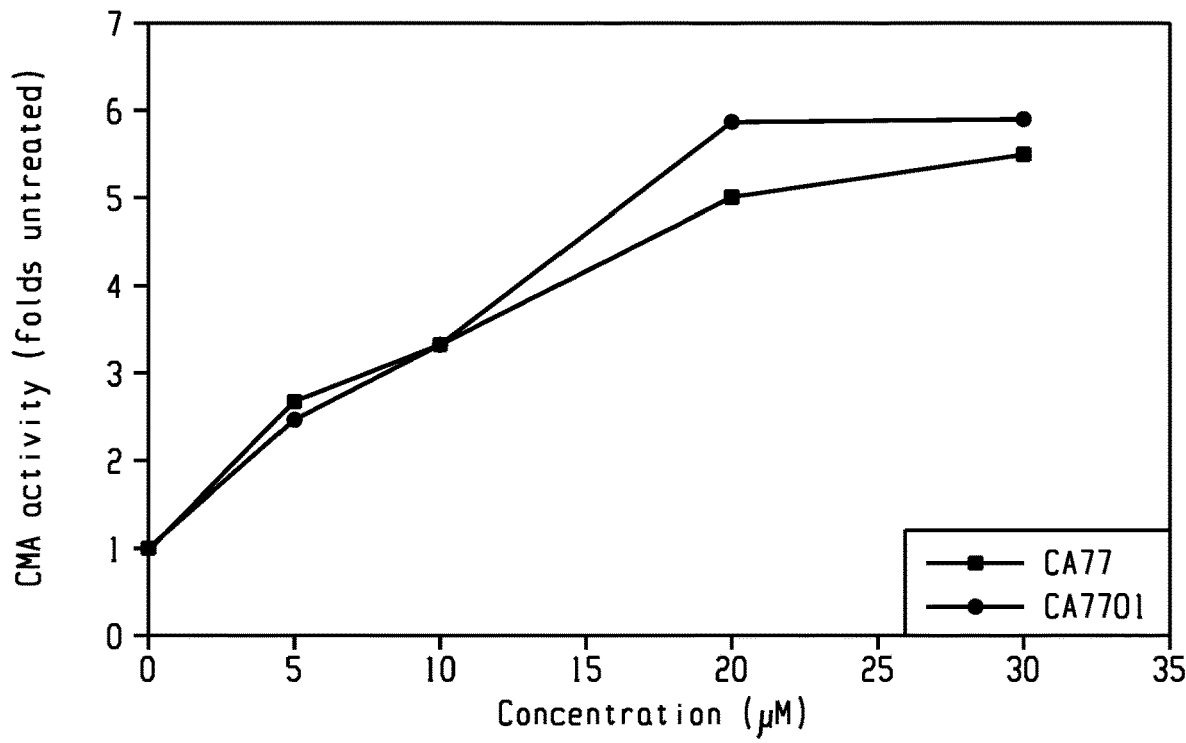

Prior to setting forth the invention in detail, it may be helpful to provide definitions of certain terms to be used in this disclosure. Compounds are described using standard nomenclature. Unless defined otherwise, all technical and scientific terms used herein have the same meaning as is commonly understood by one of skill in the art to which this invention belongs. Unless clearly contraindicated by the context each compound name includes the free acid or free base form of the compound as well as all pharmaceutically acceptable salts of the compound.

The term "compounds of Formula I" encompasses all compounds that satisfy Formula I, including any enantiomers, racemates and stereoisomers, as well as all pharmaceutically acceptable salts of such compounds. A dash that is not between two letters or symbols is used to indicate a point of attachment for a substituent.

The terms "a" and "an" do not denote a limitation of quantity, but rather denote the presence of at least one of the referenced item. The term "or" means "and/or". The open-ended transitional phrase "comprising" encompasses the intermediate transitional phrase "consisting essentially of" and the close-ended phrase "consisting of." Claims reciting one of these three transitional phrases, or with an alternate transitional phrase such as "containing" or "including" can be written with any other transitional phrase unless clearly precluded by the context or art. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in any suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

A dash ("-") that is not between two letters or symbols is used to indicate a point of attachment for a substituent. For example, —(C=O)OH is attached through carbon of the keto (C=O) group.

A bond represented by a combination of a solid and dashed line, i.e., ====, may be either a single or double bond.

"Alkyl" is a branched or straight chain saturated aliphatic hydrocarbon group, having the specified number of carbon atoms, generally from 1 to about 8 carbon atoms. The term $C_1$-$C_6$alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_4$alkyl and $C_1$-$C_2$alkyl. When $C_0$-$C_n$ alkyl is used herein in conjunction with another group, for example, —$C_0$-$C_2$alkyl(phenyl), the indicated group, in this case phenyl, is either directly bound by a single covalent bond ($C_0$alkyl), or attached by an alkyl chain having the specified number of carbon atoms, in this case 1, 2, 3, or 4 carbon atoms. Alkyls can also be attached via other groups such as heteroatoms as in —O—$C_0$-$C_4$alkyl ($C_3$-$C_7$cycloalkyl). Examples of alkyl include, but are not limited to, methyl, ethyl, n-propyl, isopropyl, n-butyl, 3-methylbutyl, t-butyl, n-pentyl, and sec-pentyl.

"Alkoxy" is an alkyl group as defined above with the indicated number of carbon atoms covalently bound to the group it substitutes by an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Aryl" indicates aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Aryl groups include, for example, phenyl, naphthyl, including 1-naphthyl, 2-naphthyl, and bi-phenyl.

"Cycloalkyl" is a saturated hydrocarbon ring group, having the specified number of carbon atoms. Monocyclic cycloalkyl groups typically have from 3 to about 7 (3, 4, 5, 6, or 7) carbon ring atoms. Cycloalkyl substituents may be pendant from a substituted nitrogen, sulfur, oxygen or carbon atom, or a substituted carbon atom that may have two substituents may have a cycloalkyl group, which is attached as a spiro group. Examples of cycloalkyl groups include cyclopropyl, cyclobutyl, cyclopentyl, or cyclohexyl as well as bridged or caged saturated ring groups such as norbornane or adamantine.

"Haloalkyl" includes both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and pentafluoroethyl.

"Haloalkoxy" is a haloalkyl group as defined herein attached through an oxygen bridge (oxygen of an alcohol radical).

"Halo" or "halogen" indicates any of fluoro, chloro, bromo, and iodo.

"Heteroaryl" is a stable monocyclic aromatic ring having the indicated number of ring atoms which contains from 1 to 4, or in some embodiments from 1 to 2, heteroatoms chosen from N, O, and S, with remaining ring atoms being carbon, or a stable bicyclic system containing at least one 5- to 7-membered aromatic ring which contains from 1 to 4, or in some embodiments from 1 to 2, heteroatoms chosen from N, O, and S, with remaining ring atoms being carbon. Monocyclic heteroaryl groups typically have from 5 to 7 ring atoms. In certain embodiments the heteroaryl group is a 5- or 6-membered heteroaryl group having 1, 2, 3, or 4 heteroatoms chosen from N, O, and S, with no more than 2 O atoms and 1 S atom.

The term "substituted," as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes aromatic moieties, the corresponding partially unsaturated ring replaces the aromatic ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. Unless otherwise specified substituents are named into the core structure. For example, it is to be understood that when aminoalkyl is listed as a possible substituent the point of attachment of this substituent to the core structure is in the alkyl portion.

In certain embodiments, groups that may be "substituted" or "optionally substituted" include, but are not limited to: monocyclic aryl, e.g., phenyl; monocyclic heteroaryl, e.g., pyrrolyl, pyrazolyl, thienyl, furanyl, imidazolyl, thiazolyl, triazolyl, pyridyl, pyrimidinyl; bicylic heteroaryl, e.g., benzimidazolyl, imidazopyridizinyl, indolyl, indazolyl, quinolinyl, isoquinolinyl; and $C_1$-$C_6$alkyl in which any carbon-carbon single bond is optionally replaced by a carbon-carbon double or triple bond, any methylene group is optionally replaced by O, S, or $NR^{12}$.

Suitable groups that may be present on a "substituted" or "optionally substituted" position include, but are not limited to: halogen; cyano; CHO; COOH; hydroxyl; oxo; amino; alkyl groups from 1 to about 6 carbon atoms; alkoxy groups having one or more oxygen linkages and from 1 to about 8, or from 1 to about 6 carbon atoms; haloalkyl groups having one or more halogens and from 1 to about 8, from 1 to about 6, or from 1 to about 2 carbon atoms; and haloalkoxy groups having one or more oxygen linkages and one or more halogens and from 1 to about 8, from 1 to about 6, or from 1 to about 2 carbon atoms.

"Pharmaceutical compositions" are compositions comprising at least one active agent, such as a compound or salt of Formula I, and at least one other substance, such as a carrier. Pharmaceutical compositions optionally contain one or more additional active agents. When specified, pharmaceutical compositions meet the U.S. FDA's GMP (good manufacturing practice) standards for human or non-human drugs.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like.

The term "carrier" applied to pharmaceutical compositions/combinations of the present disclosure refers to a diluent, excipient, or vehicle with which an active compound is provided. To be pharmaceutically acceptable a carrier must be safe, non-toxic and neither biologically nor otherwise undesirable.

Chemical Description

The disclosure provides compounds and salts of Formula I. The term "Formula I" includes the pharmaceutically acceptable salts of Formula I unless the context clearly indicates otherwise. In certain situations, the compounds of Formula I may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present disclosure. In these situations, single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example using a chiral HPFC column.

Where a compound exists in various tautomeric forms, the invention is not limited to any one of the specific tautomers, but rather includes all tautomeric forms.

The present disclosure includes all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

The disclosure includes compounds and salts of Formula I in which the variables, e.g. X, $R^1$, $R^2$, $R^3$, $R^4$, $R^5$, $R^6$, $R^7$, $R^8$, $R^9$, $R^{10}$, $R^{11}$, $R^{12}$ carry any of the definitions set forth below. Any of the variable definitions set forth below can be combined with any other of the variable definitions so long as a stable compound results.

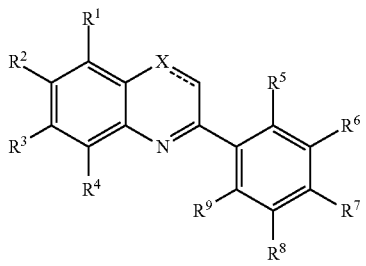

Formula I

CA77 and CA39 are provided as comparative examples and are not within the scope of Formula I.

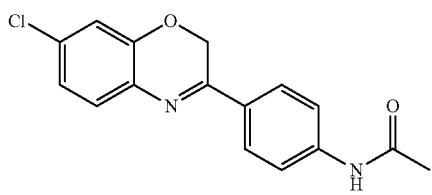

CA77

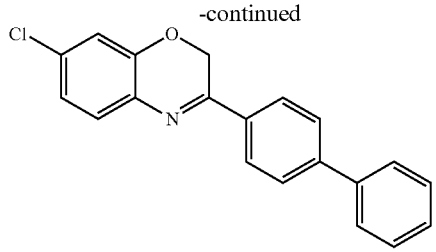

CA39

The X Variable and =====
X is O and ===== is a single bond.
X is N and ===== is an aromatic bond.
The $R^1$-$R^{12}$ Variables
(1) $R^1$, $R^3$, and $R^4$ are all hydrogen.
(2) $R^5$, $R^6$, $R^8$, and $R^9$ are all hydrogen.
(3) $R^1$, $R^3$, $R^4$, $R^5$, $R^6$, $R^8$, and $R^9$ are hydrogen.
(4) $R^2$ is chloro.
(5) $R^7$ is phenyl, napthyl, pyrrolyl, pyrazolyl thienyl, furanyl, imidazolyl, thiazolyl, triazolyl, pyridyl, pyrimidinyl, benzimidazolyl, imidazopyridizinyl, indolyl, indazolyl, quinolinyl, or isoquinolinyl, each of which is optionally substituted with one or more substituents independently chosen from halogen, hydroxyl, cyano, —CHO, —COOH, amino, and $C_1$-$C_6$alkyl in which any carbon-carbon single bond is optionally replaced by a carbon-carbon double or triple bond, any methylene group is optionally replaced by O, S, or $NR^{12}$, and optionally substituted with one or more substituents independently chosen from halogen, hydroxyl, cyano, amino, and oxo; and one substituent chosen from —$NR^{10}COR^{11}$ and $NR^{10}SO_2R^{11}$.
(6) $R^7$ is phenyl, optionally substituted with one or more substituents independently chosen from halogen, hydroxyl, $C_1$-$C_4$alkyl, $C_1$-$C_4$alkoxy, trifluoromethyl, and trifluoromethoxy; and one substituent chosen from —$NR^{10}COR^{11}$ and $NR^{10}SO_2R^{11}$.
(7) $R^7$ is phenyl, optionally substituted with one or more substituents independently chosen from hydroxyl and $C_1$-$C_2$alkoxy.
(8) $R^7$ is phenyl, optionally substituted with halogen, —$NR^{10}COR^{11}$, or $NR^{10}SO_2R^{11}$.
(9) $R^7$ is 4-fluorophenyl.
(10) $R^7$ is —$NR^{10}COR^{11}$ or —$NR^{10}SO_2R^{11}$.
(11) $R^7$ is —$NR^{10}COR^{11}$.
(12) $R^7$ is —$NR^{10}SO_2R^{11}$.
(13) $R^{10}$ is independently chosen at each occurrence from hydrogen and $C_1$-$C_6$alkyl.
(14) $R^{10}$ is hydrogen or methyl.
(15) $R^{10}$ is hydrogen.
(16) $R^{11}$ is independently chosen at each occurrence from hydrogen, $C_1$-$C_6$alkyl, $C_1$-$C_2$haloalkyl, $C_3$-$C_7$cycloalkyl, monocyclic aryl and heteroaryl, each of which monocyclic aryl and heteroaryl is optionally substituted with one or more substituents independently chosen from halogen, hydroxyl, cyano, $C_1$-$C_6$alkyl, $C_1$-$C_6$alkoxy, $C_1$-$C_2$haloalkyl, and $C_1$-$C_2$haloalkoxy.
(17) $R^{11}$ is independently chosen at each occurrence from hydrogen, $C_1$-$C_6$alkyl, $C_1$-$C_2$haloalkyl, $C_3$-$C_7$cycloalkyl, phenyl and pyridyl, each of which phenyl and pyridyl is optionally substituted with one or more substituents independently chosen from halogen, hydroxyl, cyano, $C_1$-$C_6$alkyl, $C_1$-$C_6$alkoxy, $C_1$-$C_2$haloalkyl, and $C_1$-$C_2$haloalkoxy.

(18) $R^{11}$ is chosen from $C_1$-$C_6$alkyl, $C_1$-$C_2$haloalkyl, and phenyl, each of which phenyl optionally substituted with one or more halogens.
(19) $R^{11}$ is —$C_1$-$C_6$alkyl or —$CF_3$.
(20) $R^{11}$ is —$CH_3$, $CF_3$, —$CH(CH_3)_2$, —$(CH_2)_2CH_3$, or 4-fluorophenyl.
(21) $R^{12}$ is hydrogen, $C_1$-$C_6$alkyl, or $C_3$-$C_7$cycloalkyl.
In certain embodiments $R^7$ is chosen from one of the following groups:
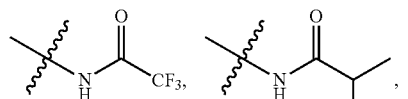
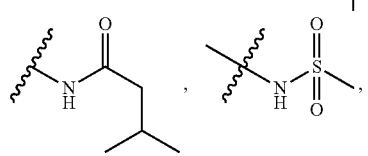
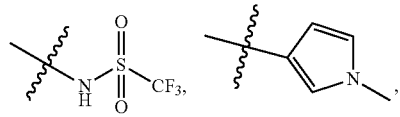
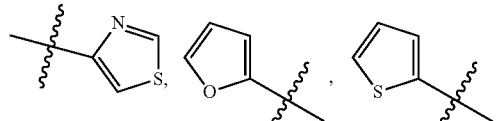
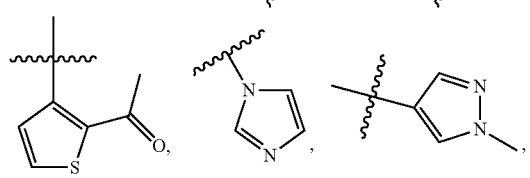
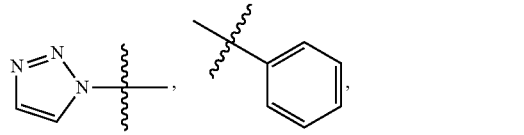
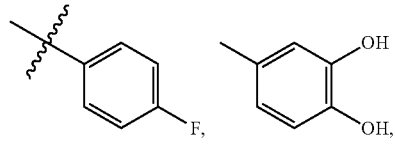
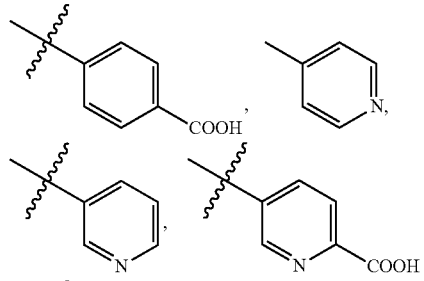
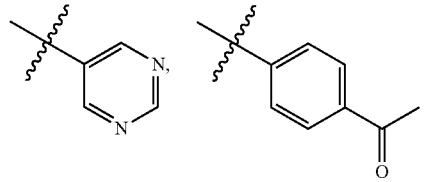
-continued
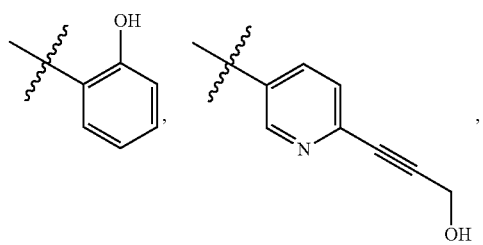
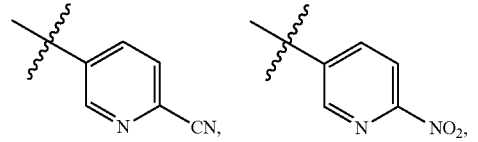
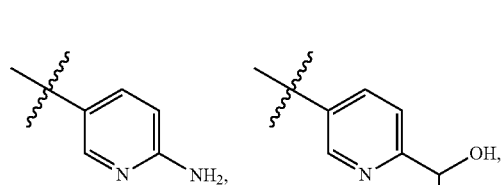
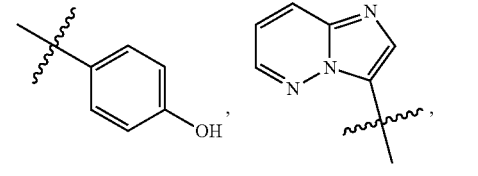
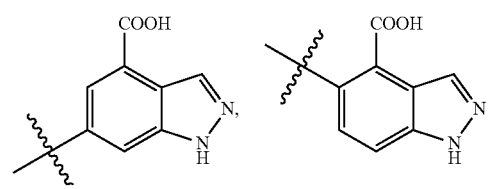
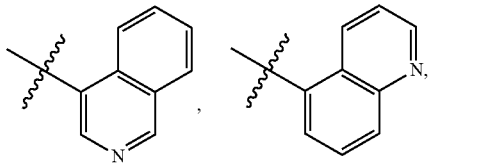
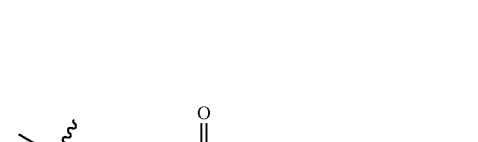
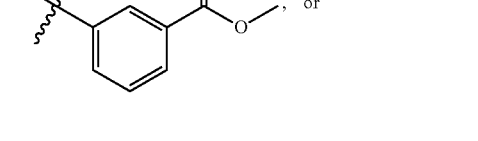

-continued

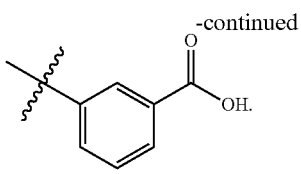

The disclosure includes the following compound and its pharmaceutically acceptable salts:

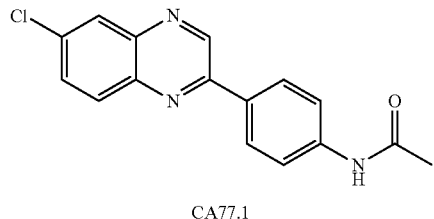 [SMILES: CC(=O)Nc1ccc(-c2cnc3cc(Cl)ccc3n2)cc1]

CA77.1

The disclosure includes the following compound and its pharmaceutically acceptable salts:

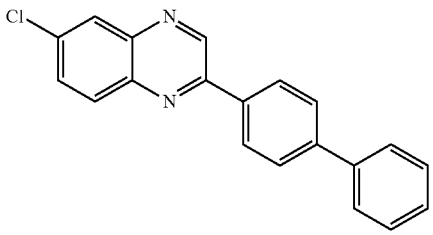

CA39.1

Certain compounds of this disclosure have advantages over comparative compounds CA77 and CA39, including improved pharmaceutical properties such as bioavailability.

Another aspect of the above embodiment (Formula I) is a compound or salt of Table 1.

TABLE 1

Benzoxazines and Quinazolines

| Cpd. No. | Chemical structure | Name |
|---|---|---|
| 1 (CA-3-55) | 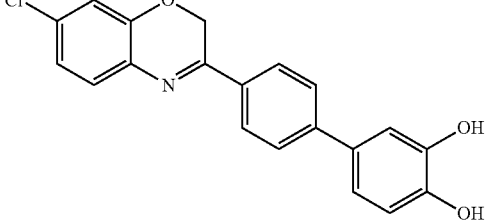 | 4'-(7-chloro-2H-benzo[b][1,4]oxazin-3-yl)-[1,1'-biphenyl]-3,4-diol |
| 2 (CA-3-67) | 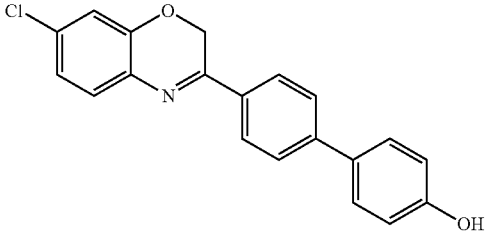 [SMILES: Oc1ccc(-c2ccc(C3=Nc4ccc(Cl)cc4OC3)cc2)cc1] | 4'-(7-chloro-2H-benzo[b][1,4]oxazin-3-yl)-[1,1'-biphenyl]-4-ol |
| 3 (CA-3-69) | 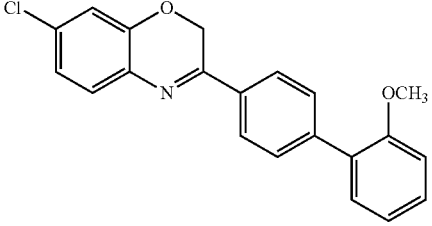 [SMILES: COc1ccccc1-c1ccc(C2=Nc3ccc(Cl)cc3OC2)cc1] | 7-chloro-3-(2'-methoxy-[1,1'-biphenyl]-4-yl)-2H-benzo[b][1,4]oxazine |
| 4 (CA-3-70) | 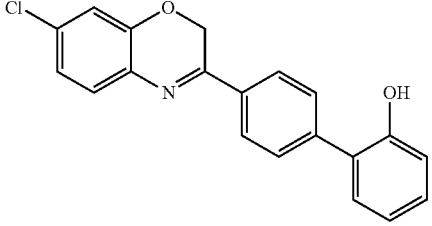 [SMILES: Oc1ccccc1-c1ccc(C2=Nc3ccc(Cl)cc3OC2)cc1] | 7-chloro-3-(2'-hydroxy-[1,1'-biphenyl]-4-yl)-2H-benzo[b][1,4]oxazine |

TABLE 1-continued

Benzoxazines and Quinazolines

| Cpd. No. | Chemical structure | Name |
| --- | --- | --- |
| 5 (CA39.1) | 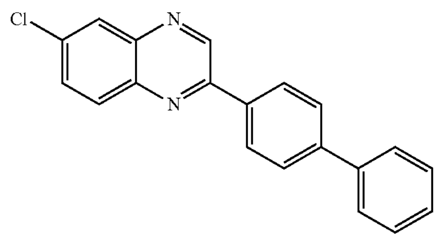 [SMILES: Clc1ccc2nc(-c3ccc(-c4ccccc4)cc3)cnc2c1] | 2-([1,1'-biphenyl]-4-yl)-6-chloroquinoxaline |
| 6 (CA77.1) | 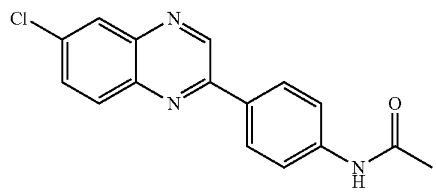 [SMILES: CC(=O)Nc1ccc(-c2cnc3cc(Cl)ccc3n2)cc1] | N-(4-(6-chloroquinoxalin-2-yl)phenyl)acetamide |
| 7 (CA77.11) | 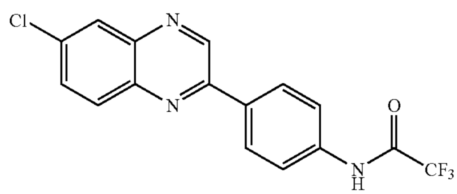 [SMILES: O=C(Nc1ccc(-c2cnc3cc(Cl)ccc3n2)cc1)C(F)(F)F] | N-(4-(6-chloroquinoxalin-2-yl)phenyl)-2,2,2-trifluoroacetamide |
| 8 (CA77.12) | 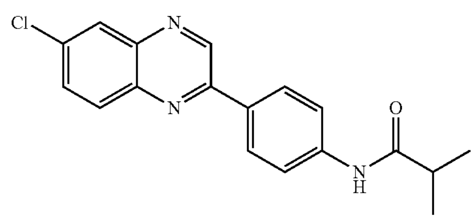 [SMILES: CC(C)C(=O)Nc1ccc(-c2cnc3cc(Cl)ccc3n2)cc1] | N-(4-(6-chloroquinoxalin-2-yl)phenyl)isobutyramide |
| 9 (CA77.13) | 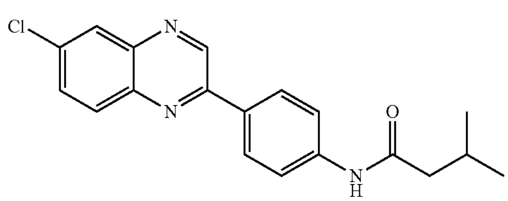 [SMILES: CC(C)CC(=O)Nc1ccc(-c2cnc3cc(Cl)ccc3n2)cc1] | N-(4-(6-chloroquinoxalin-2-yl)phenyl)butyramide |
| 10 (CA77.14) | 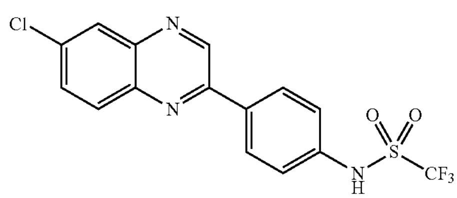 [SMILES: O=S(=O)(Nc1ccc(-c2cnc3cc(Cl)ccc3n2)cc1)C(F)(F)F] | N-(4-(6-chloroquinoxalin-2-yl)phenyl)-1,1,1-trifluoromethanesulfonamide |
| 11 (CA77.15) | 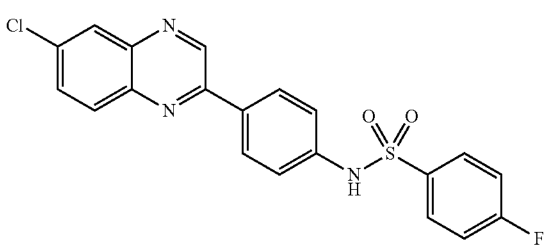 [SMILES: O=S(=O)(Nc1ccc(-c2cnc3cc(Cl)ccc3n2)cc1)c1ccc(F)cc1] | N-(4-(6-chloroquinoxalin-2-yl)phenyl)-4-fluorobenzenesulfonamide |

TABLE 1-continued

Benzoxazines and Quinazolines

| Cpd. No. | Chemical structure | Name |
| --- | --- | --- |
| 12 (CA77.16) | 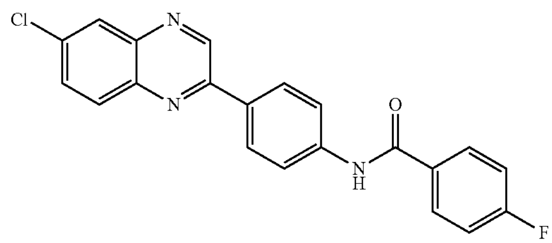 [SMILES: O=C(Nc1ccc(-c2cnc3cc(Cl)ccc3n2)cc1)c1ccc(F)cc1] | N-(4-(6-chloroquinoxalin-2-yl)phenyl)-4-fluorobenzamide |
| 13 (CA39.12) | 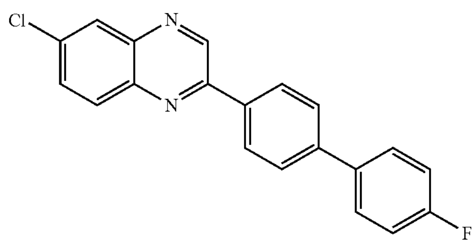 [SMILES: Fc1ccc(-c2ccc(-c3cnc4cc(Cl)ccc4n3)cc2)cc1] | 6-chloro-2-(4'-fluoro-[1,1'-biphenyl]-4-yl)quinoxaline |
| 14 (CA39.13) | 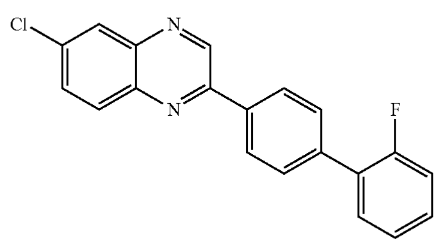 [SMILES: Fc1ccccc1-c1ccc(-c2cnc3cc(Cl)ccc3n2)cc1] | 6-chloro-2-(2'-fluoro-[1,1'-biphenyl]-4-yl)quinoxaline |
| 15 (CA39.14) | 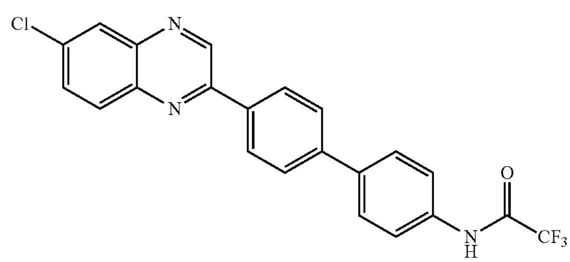 [SMILES: O=C(Nc1ccc(-c2ccc(-c3cnc4cc(Cl)ccc4n3)cc2)cc1)C(F)(F)F] | N-(4'-(6-chloroquinoxalin-2-yl)-[1,1'-biphenyl]-4-yl)-2,2,2-trifluoroacetamide |
| 16 (CA39.15) | 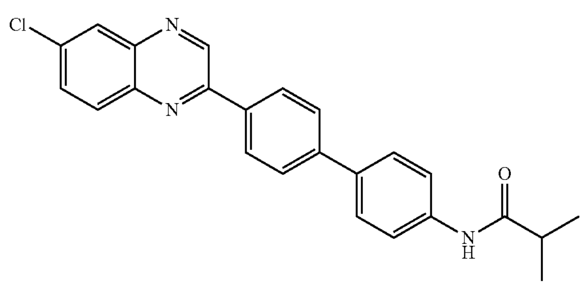 [SMILES: CC(C)C(=O)Nc1ccc(-c2ccc(-c3cnc4cc(Cl)ccc4n3)cc2)cc1] | N-(4'-(6-chloroquinoxalin-2-yl)-[1,1'-biphenyl]-4-yl)isobutyramide |
| 17 (CA39.16) | 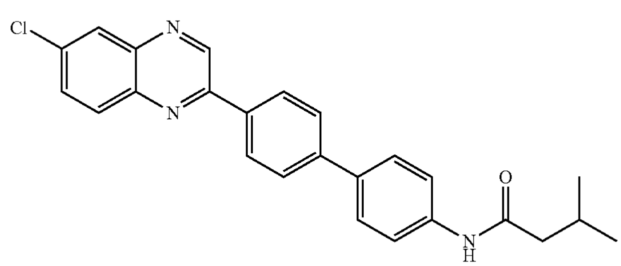 [SMILES: CC(C)CC(=O)Nc1ccc(-c2ccc(-c3cnc4cc(Cl)ccc4n3)cc2)cc1] | N-(4'-(6-chloroquinoxalin-2-yl)-[1,1'-biphenyl]-4-yl)butyramide |

TABLE 1-continued

Benzoxazines and Quinazolines

| Cpd. No. | Chemical structure | Name |
|---|---|---|
| 18 (CA39.17) | 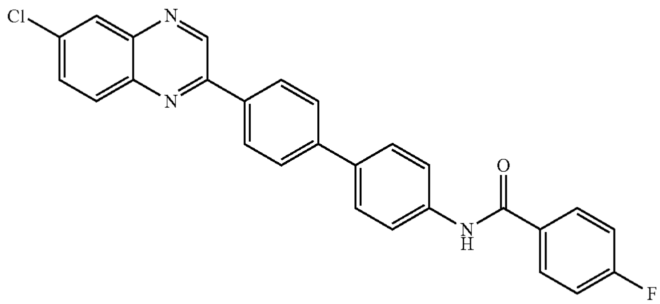 [SMILES: O=C(Nc1ccc(-c2ccc(-c3cnc4cc(Cl)ccc4n3)cc2)cc1)c1ccc(F)cc1] | N-(4'-(6-chloroquinoxalin-2-yl)-[1,1'-biphenyl]-4-yl)-4-fluorobenzamide |
| 19 (CA39.18) | 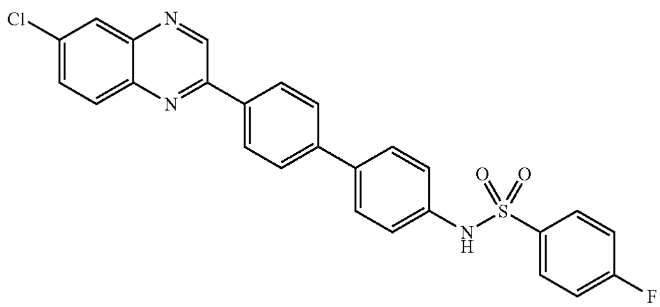 [SMILES: O=S(=O)(Nc1ccc(-c2ccc(-c3cnc4cc(Cl)ccc4n3)cc2)cc1)c1ccc(F)cc1] | N-(4'-(6-chloroquinoxalin-2-yl)-[1,1'-biphenyl]-4-yl)-4-fluorobenzenesulfonamide |
| 20 (CA39.19) | 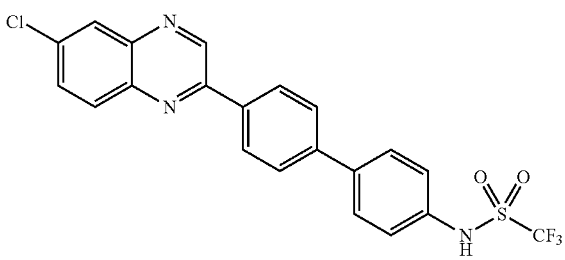 [SMILES: O=S(=O)(Nc1ccc(-c2ccc(-c3cnc4cc(Cl)ccc4n3)cc2)cc1)C(F)(F)F] | N-(4'-(6-chloroquinoxalin-2-yl)-[1,1'-biphenyl]-4-yl)-1,1,1-trifluoromethanesulfonamide |

Pharmaceutical Preparations

Compounds disclosed herein can be administered as the neat chemical, but are preferably administered as a pharmaceutical composition. Accordingly, the disclosure provides pharmaceutical compositions comprising a compound or pharmaceutically acceptable salt of a CMA modulator, such as a compound of Formula I, together with at least one pharmaceutically acceptable carrier. In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of a compound of Formula I and optionally from about 0.1 mg to about 2000 mg, from about 10 mg to about 1000 mg, from about 100 mg to about 800 mg, or from about 200 mg to about 600 mg of an additional active agent in a unit dosage form.

Compounds disclosed herein may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present disclosure.

The pharmaceutical compositions/combinations can be formulated for oral administration. These compositions contain between 0.1 and 99 weight % (wt. %) of a compound of Formula I and usually at least about 5 wt. % of a compound of Formula I. Some embodiments contain from about 25 wt. % to about 50 wt. % or from about 5 wt. % to about 75 wt. % of the compound of Formula.

Methods of Treatment

The disclosure also provides methods of selectively activating chaperone-mediated autophagy (CMA) in a subject in need thereof comprising administering to the subject a compound of Formula I in an amount effective to activate CMA in the subject.

The subject can have, for example, a neurodegenerative disease, such as tauopathies, (Frontotemporal Dementia, Alzheimer's disease), Parkinson's Disease, Huntington's Disease, prion diseases, amyotrophic lateral sclerosis, retinal degeneration, leber congenital amaurosis, diabetes, acute liver failure, non-alcoholic steatohepatitis (NASH), hepatosteatosis, alcoholic fatty liver, renal failure and chronic kidney disease, emphysema, sporadic inclusion body myositis, spinal cord injury, traumatic brain injury, a lysosomal storage disorder, a cardiovascular disease, and immunosenescence. Lysosomal storage disorders include, but are not limited to, cystinosis, galactosialidosis, and mucolipidosis. The subject may also have a disease or condition in which CMA is upregulated such as cancer or Lupus. The subject can have reduced CMA compared to a normal subject prior to administering the compound. Preferably, the compound does not affect macroautophagy or other autophagic pathways. In macrophagy, proteins and organelles are sequestered in double-membrane vesicles and delivered to lysosomes for degradation. In CMA, protein substrates are selectively identified and targeted to the lysosome via interactions with a cytosolic chaperone.

The disclosure also provides a method of protecting cells from oxidative stress, proteotoxicity and/or lipotoxicity in a subject in need thereof comprising administering to the subject any of the compounds disclosed herein, or a combination of a compound of Formula I, in an amount effective to protect cells from oxidative stress, proteotoxicity and/or lipotoxicity. The subject can have, for example, one or more of the chronic conditions that have been associated with increased oxidative stress and oxidation and a background of propensity to proteotoxicity. The cells being protected can comprise, for example, cardiac cells, kidney and liver cells, neurons and glia, myocytes, fibroblasts and/or immune cells. The compound can, for example, selectively activate chaperone-mediated autophagy (CMA). In one embodiment, the compound does not affect macroautophagy.

In an embodiment the subject is a mammal. In certain embodiments the subject is a human, for example a human patient undergoing medical treatment. The subject may also be a companion a non-human mammal, such as a companion animal, e.g. cats and dogs, or a livestock animal.

For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids (e.g., blood, plasma, serum, cellular interstitial fluid, saliva, feces and mine) and cell and tissue samples of the above subjects will be suitable for use.

An effective amount of a pharmaceutical composition may be an amount sufficient to inhibit the progression of a disease or disorder, cause a regression of a disease or disorder, reduce symptoms of a disease or disorder, or significantly alter a level of a marker of a disease or disorder. For example levels of dopamine transporter (DAT) and vesicular monoamine transporter 2 (VMAT2) are both reduced in the brains of Parkinson's sufferers in the prodromal phase and at diagnosis and are may also be used to monitor disease progression by brain imaging. Thus a therapeutically effective amount of a compound of Formula I includes an amount effect to slow the decrease in brain DAT or VMAT2 levels as observed by brain imaging. Accumulation of Tau protein in brains of frontotemporal dementia patients has been observed by PET imaging, thus a therapeutically effective amount of a compound of Formula I includes and amount sufficient to decrease tau brain deposits or slow the rate of tau brain deposition. Markers for effective treatment of NASH, hepatosteatosis, and alcoholic fatty liver include reduced lipid content and fibrosis in liver biopsy. Markers for effective treatment of cancer include reduced tumor size, for example as observed by MRI, reduced number or size of metastasis. Markers for effective treatment of emphysema include improved volumetric and speed parameters in spirometry. Markers for effective treatment of immunosenescence include recover T cell activation in vitro. Markers for effective treatment of kidney malfunction include normalization of plasma creatine levels and plasma to urine creatine ratio.

An effective amount of a compound or pharmaceutical composition described herein will also provide a sufficient concentration of a compound of Formula I when administered to a subject. A sufficient concentration is a concentration of the compound of Formula I in the patient's body necessary to prevent or combat a CMA mediated disease or disorder or other disease ore disorder for which a compound of Formula I is effective. Such an amount may be ascertained experimentally, for example by assaying blood concentration of the compound, or theoretically, by calculating bioavailability.

Methods of treatment include providing certain dosage amounts of a compound of Formula I to a subject or patient. Dosage levels of each compound of from about 0.1 mg to about 140 mg per kilogram of body weight per day are useful in the treatment of the above-indicated conditions (about 0.5 mg to about 7 g per patient per day). The amount of compound that may be combined with the carrier materials to produce a single dosage form will vary depending upon the patient treated and the particular mode of administration. Dosage unit forms will generally contain between from about 1 mg to about 500 mg of each active compound. In certain embodiments 25 mg to 500 mg, or 25 mg to 200 mg of a compound of Formula I are provided daily to a patient. Frequency of dosage may also vary depending on the compound used and the particular disease treated. However, for treatment of most diseases and disorders, a dosage regimen of 4 times daily or less can be used and in certain embodiments a dosage regimen of 1 or 2 times daily is used.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

In an embodiment, the invention provides a method of treating a lysosomal storage disorder in a patient identified as in need of such treatment, the method comprising providing to the patient an effective amount of a compound of Formula I. The compounds of Formula I provided herein may be administered alone as the only active agent, or in combination with one or more other active agent.

EXAMPLES

Examples 1-3 provide detailed synthetic methods for representative compounds. Remaining compounds of this disclosure can be made by these methods using changes in starting materials and reaction conditions that will be readily apparent to those of ordinary skill in the art of organic chemistry synthesis.

Example 1. Synthesis of N-(4-(6-chloroquinoxalin-2-yl)phenyl)acetamide (CA77.1)

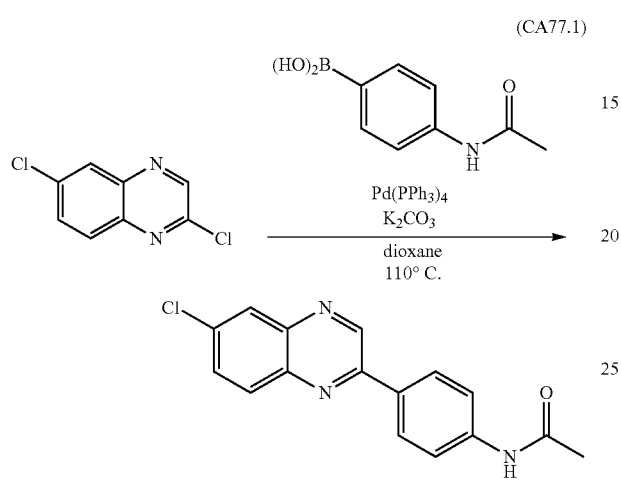

In a dry and Argon-flushed 50 mL round-bottom flask, 2,6-dichloroquinoxaline (250 mg, 1.25 mmol), (4-acetamidophenyl)boronic acid (293 mg, 1.64 mmol, 1.30 equiv), and potassium carbonate (1.0 M; 1.25 mL, 1.25 mmol, 1.00 equiv) were dissolved in dioxane (8.40 mL). The mixture was degassed (argon bubbling for 20 min). Palladium tetrakis (73 mg, 63 μmol, 5.0 mol-%), was then added. The flask was purged with more argon and a reflux condenser was placed on top. The mixture was heated under an argon atmosphere at 100° C. overnight. TLC analysis indicated complete conversion. The mixture was filtered; the resulting solid was purified using combiFlash (MeOH in DCM gradient 0-10%). The product was recrystallized using dichloromethane and methanol mixture.

TLC: $R_f$=0.16 (2% MeOH in $CH_2Cl_2$). $^1$H-NMR (600 MHz, dmso-$d_6$): 10.20 (s, 1H), 9.58 (s, 1H), 8.32-8.31 (m, 2H), 8.18 (d, J=2.4 Hz, 1H), 8.13 (d, J=8.9 Hz, 1H), 7.89 (dd, J=8.9, 2.4 Hz, 1H), 7.82 (d, J=8.8 Hz, 2H), 2.11 (s, 3H). $^{13}$C-NMR (151 MHz, CDCl$_3$): δ 168.6, 150.9, 144.5, 141.6, 141.0, 140.1, 133.5, 131.0, 130.8, 129.9, 128.1, 127.5, 119.0, 24.1. HRMS (for $C_{16}H_{12}ClN_3O$, M+H): calculated: 298.0742, found: 298.0743.

Example 2. Synthesis of 3-([1,1'-biphenyl]-4-yl)-7-chloro-2H-benzo[b][1,4]oxazine (CA39)

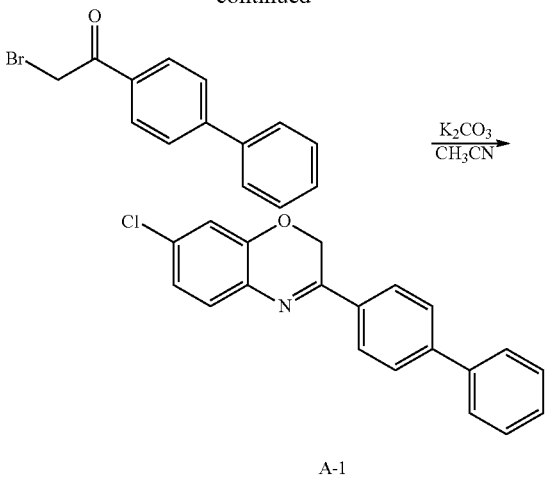

To 2-amino-5-chlorophenol (1 g, 6.96 mmol) in acetonitrile (40 mL) was added $K_2CO_3$ (1.92 g, 13.92 mmol). 1-([1,1'-biphenyl]-4-yl)-2-bromoethan-1-one (2.15 g, 8.36 mmol) in acetonitrile (20 mL) was added dropwise at room temperature to this mixture. The reaction mixture was then stirred overnight at room temperature. The solvent was then evaporated and the residue was dissolved in dichloromethane (20 mL). The organic layer was washed with water, brine, and dried over $Na_2SO_4$. The desired compound was isolated through silica gel chromatography (hexanes/ethyl acetate: 15/1). Recrystallization with isopropanol gave a light yellow powder (A-1, CA39, 1.2 g, 53.9%).

$^1$H-NMR (300M, CDCl$_3$) δ ppm: 8.03 (d, J=0.03 Hz, 2H), 7.75 (d, J=0.02 Hz, 2H), 7.68 (d, J=0.02 Hz, 2H), 7.48-7.53 (m, 2H), 7.37-7.45 (m, 2H), 7.01-7.05 (dd, J=0.01 Hz, 0.03 Hz, 1H), 6.96 (d, J=0.01 Hz, 1H), 5.13 (s, 2H). $^{13}$C-NMR (151 MHz, DMSO-d6) δ ppm: 158.11, 146.84, 144.08, 140.00, 133.90, 133.30, 132.48, 128.95×2, 128.51, 128.05, 127.44×2, 127.15×2, 126.94×2, 62.83. 1HRMS: calculated for $C_{20}H_{14}ClNO$ (M+H) 320.0837, found: 320.0839.

Example 3. Synthesis of 2-([1,1'-biphenyl]-4-yl)-6-chloroquinoxaline (CA39.1)

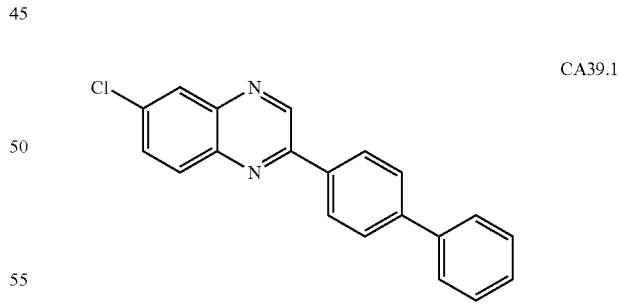

A nitrogen flushed vessel was filled with 2,6-dichloroquinoxaline (200 mg, 1 mmol), (4-acetamidophenyl)boronic acid (1257.4 mg, 1.3 mmol), and $K_2CO_3$ (276 mg, 2 mmol, 2N in water). The vessel was flushed with nitrogen for a second time and tetrakis(triphenylphosphine)palladium(0) (115.6 mg, 0.1 mmol) was added. Then solvent dioxane (10 mL) was added and the reaction was degassed and protected with nitrogen, and stirred at 110° C. overnight. Then the solvent was evaporated and the residue was loaded to silica gel for purification (hexanes/acetone: 5/1-2/1). Then the obtained crude product was recrystallized with hot ethanol to give a light yellow powder (CA39.1, 181.3 mg, 57%).

$^1$H-NMR (300M, CDCl$_3$) δ ppm: 9.41 (s, 1H), 8.33 (d, J=0.03 Hz, 2H), 8.15 (d, J=0.03 Hz, 2H), 7.85 (d, J=0.03 Hz, 2H), 7.75-7.78 (dd, J$_1$=0.03 Hz, J$_2$=0.01 Hz, 2H), 7.72 (d, J=0.02 Hz, 2H), 7.50-7.55 (m, 2H), 7.46 (d, J=0.03 Hz, 1H). $^{13}$C-NMR (75 MHz, CDCl$_3$) δ ppm: 151.60, 144.14, 143.31, 141.91, 141.00, 140.21, 135.30, 135.25, 131.44, 130.91, 129.03×2, 128.18, 127.99×2, 127.98×2, 127.24×2. HRMS: calculated for C$_{20}$H$_{13}$ClN$_2$ (M+H) 317.0840, found: 317.0839.

Example 4. Measurement of CMA Activity In Vitro

The photoactivatable CMA reporter assay was constructed by inserting a sequence of 21 amino acid of Ribonuclease A bearing the CMA-targeting motif in the N-terminus multicloning site of the photoactivatable protein mCherryl or the photoswitchable protein Dendra 2.

Figure 3A:
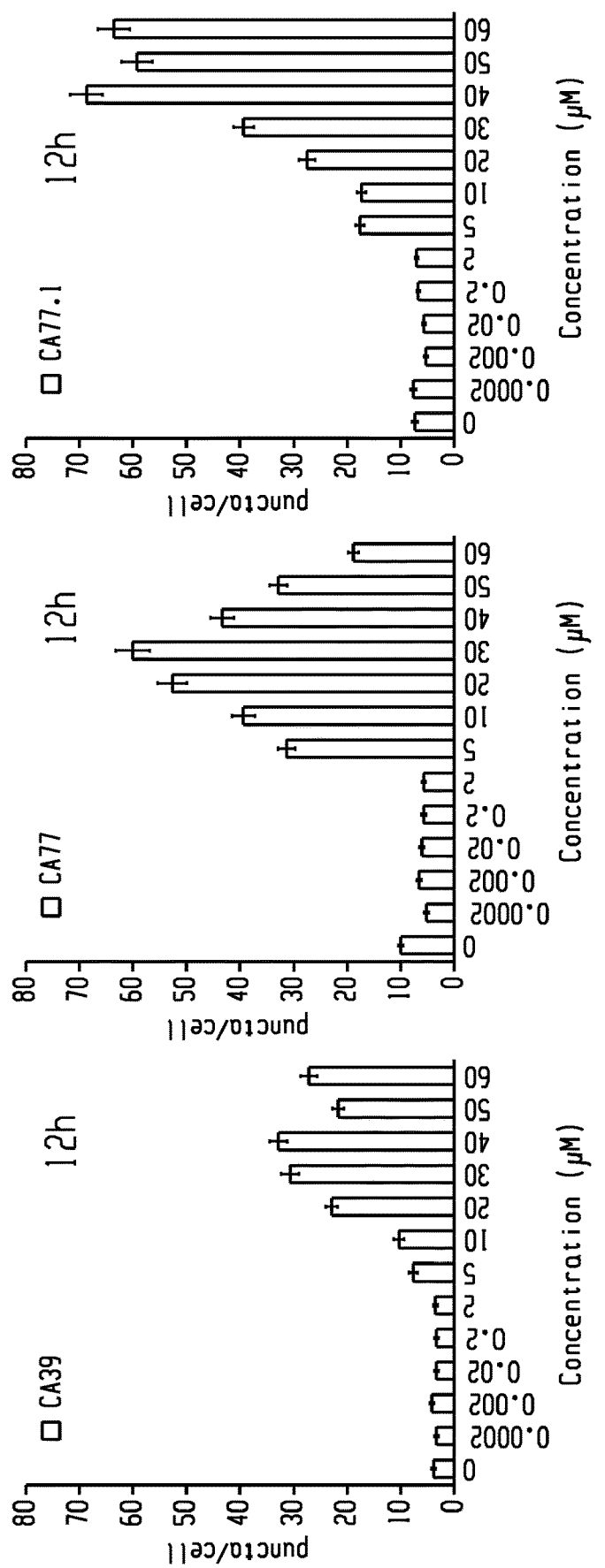
FIGS. 3A-3B.
Figure 3B:
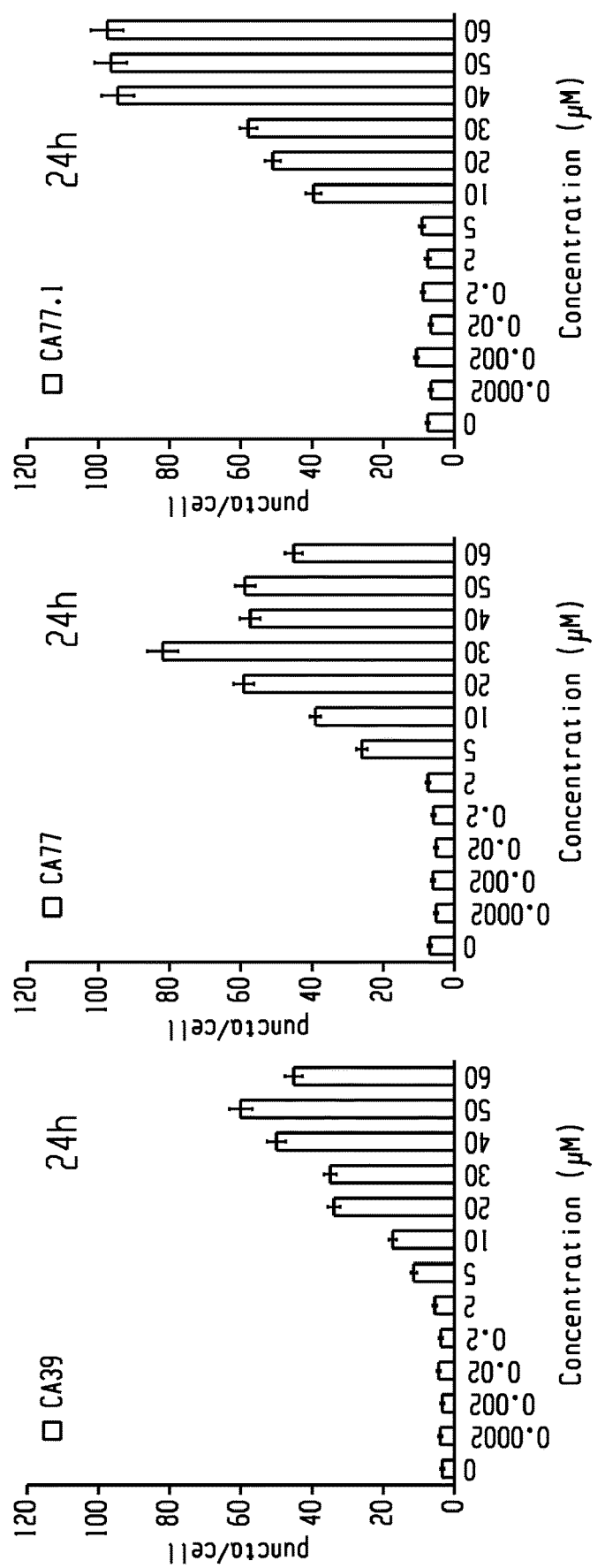

NIH 3T3 fibroblasts were stably transduced with a photoconvertible CMA reporter, KFERQ-Dendra. were photoswitched by exposure to a 3.5 MA (constant current) LED (Norlux, 405 nm) for 10 minutes and at the desired times fixed in 3% formaldehyde. Test cells were exposed to the indicated concentrations of the compounds for 12 hours (FIG. 3A) or 24 hours (FIG. 3B). Cells were imaged using high content microscopy (Operetta, Perkin Elmer) or by capturing images with an Axiovert 200 fluorescence microscope (Zeiss) with apotome and equipped with a 63/1.4 NA oil objective lens and red (ex. 570/30 nm, em. 615/30 nm), cyan (ex. 365/50 nm and em. 530/45 nm) and green (ex. 475/40 nm and em. 535/45 nm) filter sets (Chroma). Images were acquired with a high-resolution CCD camera after optical sectioning through the apotome. CMA activity measured as the average number of fluorescent puncta (CMA active lysosomes) per cell. Values are expressed relative to values in untreated cells that were assigned an arbitrary value of 1 and are mean of >2,500 cells counted per condition. The S.D. in all instances was <0.01% mean value. Table 2 provides a comparison of compounds CA39.1 and its comparative example CA39 and CA77.01 and its comparative example CA77.

TABLE 2

| Time | CA39 | CA39.1 | CA77 | CA77.1 |
|---|---|---|---|---|
| 0 | 1 | 1 | 1 | 1 |
| 5 | 2.457287 | 2.106733 | 2.66694 | 2.529802 |
| 10 | 2.619221 | 2.232819 | 3.331226 | 3.364937 |
| 20 | 3.586779 | 2.605309 | 5.005261 | 5.857794 |
| 30 | 4.373779 | 2.924662 | 5.471211 | 5.889334 |

Example 5. Pharmacokinetics Comparison for CA77 and CA77.1

All animal work was approved and performed according to the guidelines set by the Albert Einstein College of Medicine Institutional Animal Care and Use Committee.

Figure 2A:
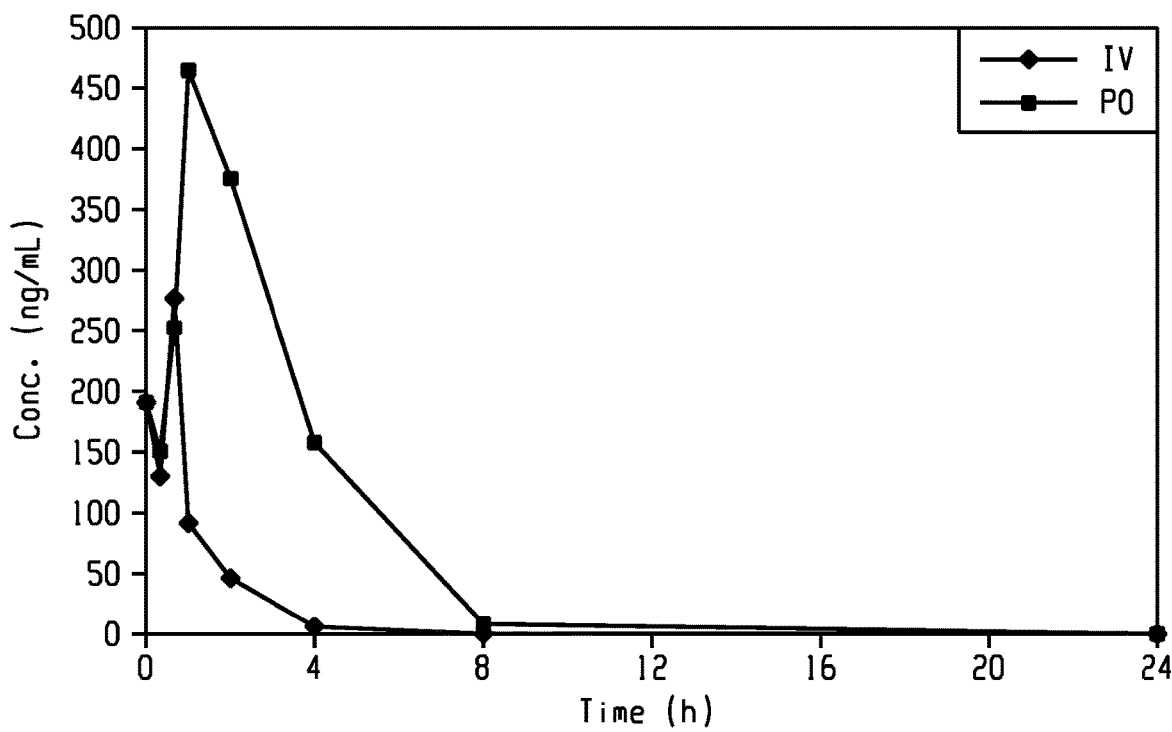
FIGS. 2A-2B.
Figure 2B:
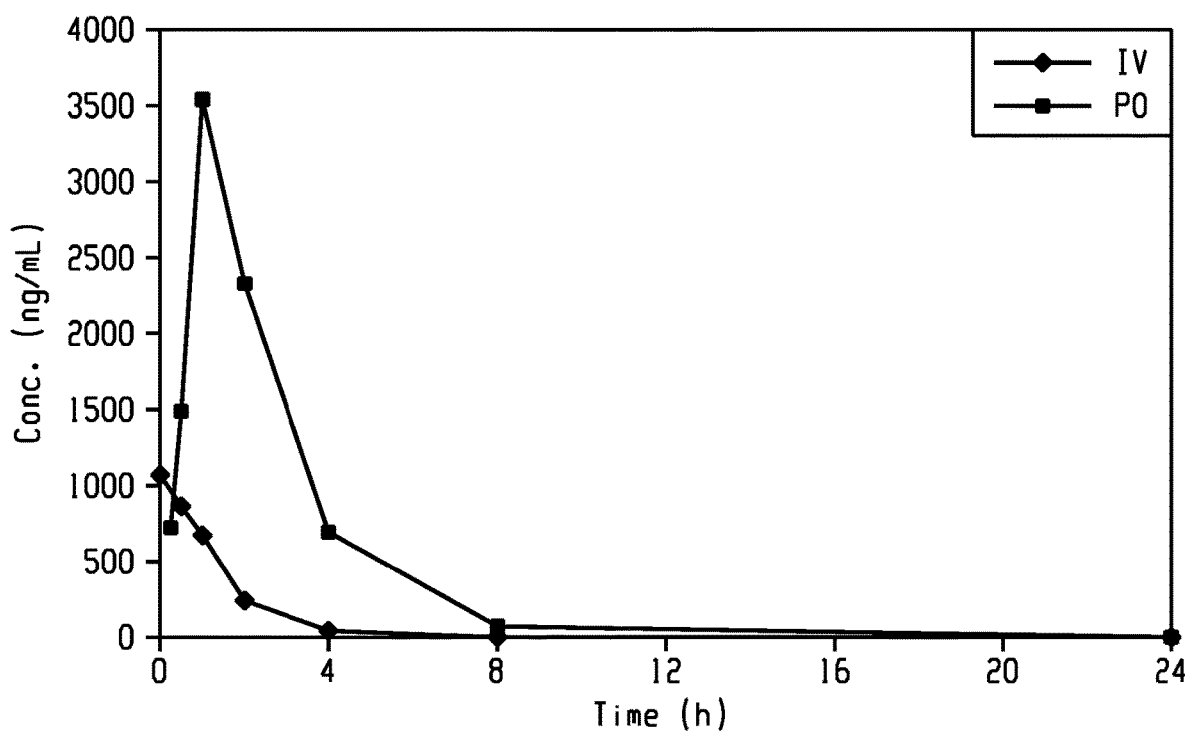

ICR (CD-1) male mice were fasted at least three horns and water was available ad libitum before the study. Animals were housed in a controlled environment, target conditions: temperature 18 to 29° C., relative humidity 30 to 70%. Temperature and relative humidity was monitored daily. An electronic time controlled lighting system was used to provide a 12 h light/12 h dark cycle. 3 mice for each indicated time point. ICR (CD-1) mice were administered CA77 at 1 mg/kg i.v. and 30 mg/kg p.o. or CA77.1 at 1 mg/kg i.v. (FIG. 2A) and 10 mg/kg p.o. (FIG. 2B). Three (3) mice were included in each dosage and time group. Mice were sacrificed and plasma and brains were obtained at 0.083, 0.25, 0.50, 1.0, 2.0, 4.0, 8.0, and 24.0 hours after administration and drug concentration determined using LC-MS/MS. Brains were removed, homogenized with a tissue homogenizer in cold 5% w/v BSA in phosphate buffer saline (PBS). A 100 microliter aliquots of brain samples were dispensed in to glass culture tubes and mixed with ethyl acetate (800 μl), vortexed, and centrifuged. The organic layer was transferred to a fresh culture tube, dried under nitrogen, and reconstituted in mobile phase for quantitation. Pharmacokinetic parameters were determined by standard methods using Phoenix WinNonlin 6.3 software.

Tables 3A and 3B provide the concentrations of CA77 in ICR (CD-1) mouse plasma (3A) and mouse brain (3B) following i.v. administration of 1 mg/kg CA77. Table 3C provides the brain/plasma ratio of CA77 following i.v. administration of 1 mg/kg CA77. The plasma and brain pharmacokinetic parameters for CA77 are provided in Table 4. Shaded cells indicate data not included in statistics due to aberrant value. BLQ=Below Limit of Quantitation.

TABLE 3A

| Time (h) | Conc. (ng/mL) | Mean | SD | CV(%) |
|---|---|---|---|---|
| 0.083 | 52.9 | 47.1 | — | — |
|  | 41.4 |  |  |  |
|  | *14 |  |  |  |
| 0.25 | 27.2 | 30.2 | 12.5 | 41.4 |
|  | 43.9 |  |  |  |
|  | 19.5 |  |  |  |
| 0.50 | 17.2 | 17.9 | 3.73 | 20.8 |
|  | 14.6 |  |  |  |
|  | 21.9 |  |  |  |
| 1.00 | 15.5 | 15.4 | 3.54 | 23.0 |
|  | 21.5 |  |  |  |
|  | 15.3 |  |  |  |
| 2.00 | 7.54 | 4.37 | 2.95 | 67.6 |
|  | 1.71 |  |  |  |
|  | 3.84 |  |  |  |
| 4.00 | BLQ | 0.565 | — | — |
|  | 0.597 |  |  |  |
|  | 0.533 |  |  |  |

TABLE 3B

| Time (h) | Conc. (ng/g) | Mean | SD | CV(%) |
|---|---|---|---|---|
| 0.083 | 3773 | 3357.8 | — | — |
|  | 2943 |  |  |  |
|  | *693 |  |  |  |
| 0.25 | 3391 | 3654 | 1407 | 38.5 |
|  | 5173 |  |  |  |
|  | 2397 |  |  |  |
| 0.50 | 2198 | 2648 | 397 | 15.0 |
|  | 2795 |  |  |  |
|  | 2950 |  |  |  |
| 1.00 | 2758 | 2456 | 322 | 13.1 |
|  | 2651 |  |  |  |
|  | 2154 |  |  |  |
| 2.00 | 773 | 659 | 215 | 32.6 |
|  | 411 |  |  |  |
|  | 792 |  |  |  |
| 4.00 | 76.0 | 104 | 24.9 | 24.0 |
|  | 112 |  |  |  |
|  | 124 |  |  |  |

TABLE 3B-continued

| Time (h) | Conc. (ng/g) | Mean | SD | CV(%) |
|---|---|---|---|---|
| 8.00 | 7.74 | 25.6 | 16.9 | 66.2 |
|  | 27.5 |  |  |  |
|  | 41.4 |  |  |  |
| 24.0 | 2.68 | 3.00 | 1.12 | 37.5 |
|  | 4.25 |  |  |  |
|  | 2.07 |  |  |  |

TABLE 3C

| Time (h) | Brain/Plasma | Mean | SD | CV(%) |
|---|---|---|---|---|
| 0.083 | 71.3 | 71.2 | — | — |
|  | 71.1 |  |  |  |
|  | *48.9 |  |  |  |
| 0.25 | 125 | 122 | 3.6 | 3.0 |
|  | 118 |  |  |  |
|  | 123 |  |  |  |
| 0.50 | 128 | 151 | 35.2 | 23.3 |
|  | 192 |  |  |  |
|  | 135 |  |  |  |
| 1.00 | 178 | 159 | 27.8 | 17.5 |
|  | 123 |  |  |  |
|  | 141 |  |  |  |
| 2.00 | 102 | 183 | 71.7 | 39.2 |
|  | 240 |  |  |  |
|  | 206 |  |  |  |
| 4.00 | — | 210 | — | — |
|  | 188 |  |  |  |
|  | 232 |  |  |  |

TABLE 4

Pharmacokinetics parameters of QX77 after p.o. and i.v. administration in ICR (CD-1) mice

|  | $T_{1/2}$ (h) | $T_{max}$ (h) | $C_{max}$ (ng/mL) | $AUC_{last}$ (h * ng/mL) | $AUC_{INF\_obs}$ (h * ng/mL) |
|---|---|---|---|---|---|
| p.o. | 2.19 | 2.00 | 278 | 1317 | 1458 |
| i.v. | 0.635 | 0.0830 | 36.2 | 35.3 | 35.8 |

|  | $CL_{\_obs}$ (mL/min/kg) | $MRT_{INF\_obs}$ (h) | $VSS_{\_obs}$ (mL/kg) | F % |
|---|---|---|---|---|
| p.o. | 343 | 3.97 | — | 124 |
| i.v. | 465 | 0.952 | 26548 |  |

Tables 5A and 5B provide the concentrations of CA77.1 in ICR (CD-1) mouse plasma (5A) and mouse brain (5B) following i.v. administration of 1 mg/kg CA77.1. Table 5C provides the brain/plasma ratio of CA77.1 following i.v. administration of 1 mg/kg CA77.1. The plasma and brain pharmacokinetic parameters for CA77.1 are provided in Table 6. *—cells contain data not present in the statistics.

TABLE 5A

| Time (h) | Conc. (ng/mL) | Mean | SD | CV(%) |
|---|---|---|---|---|
| 0.083 | 177 | 190 | 21 | 11 |
|  | 178 |  |  |  |
|  | 214 |  |  |  |
| 0.25 | 132 | 129 | 24 | 19 |
|  | 152 |  |  |  |
|  | 104 |  |  |  |
| 0.50 | 247 | 276 | 192 | 70 |
|  | 100 |  |  |  |
|  | 481 |  |  |  |
| 1.00 | 110 | 91 | 16 | 18 |
|  | 79.3 |  |  |  |
|  | 85.0 |  |  |  |
| 2.00 | 30.8 | 46 | 20 | 44 |
|  | 38.5 |  |  |  |
|  | 69.4 |  |  |  |
| 4.00 | 3.31 | 6 | 4 | 71 |
|  | 3.33 |  |  |  |
|  | 10.2 |  |  |  |
| 8.00 | 2.74 | 2 | 1 | 41 |
|  | 1.43 |  |  |  |
|  | 1.42 |  |  |  |
| 24.0 | 0.556 | 1 | — | — |
|  | *7.61 |  |  |  |
|  | *16.6 |  |  |  |

TABLE 5B

| Time (h) | Conc. (ng/g) | Mean | SD | CV(%) |
|---|---|---|---|---|
| 0.083 | 1031 | 1057 | 103 | 10 |
|  | 1171 |  |  |  |
|  | 970 |  |  |  |
| 0.25 | 864 | 789 | 88 | 11 |
|  | 813 |  |  |  |
|  | 691 |  |  |  |
| 0.50 | 677 | 812 | 234 | 29 |
|  | 677 |  |  |  |
|  | 1083 |  |  |  |
| 1.00 | 597 | 669 | 99 | 15 |
|  | 628 |  |  |  |
|  | 781 |  |  |  |
| 2.00 | 276 | 244 | 50 | 21 |
|  | 269 |  |  |  |
|  | 186 |  |  |  |
| 4.00 | 18.2 | 19 | 6 | 30 |
|  | 13.6 |  |  |  |
|  | 24.9 |  |  |  |
| 8.00 | 4.92 | 4 | 1 | 21 |
|  | 3.31 |  |  |  |
|  | 3.66 |  |  |  |
| 24.0 | 0 | 0 | 0 | — |
|  | 0 |  |  |  |
|  | 0 |  |  |  |

TABLE 5C

| Time (h) | Brain/Plasma | Mean | SD | CV(%) |
|---|---|---|---|---|
| 0.083 | 5.81 | 5.64 | 1.03 | 18.2 |
| | 6.57 | | | |
| | 4.53 | | | |
| 0.25 | 6.54 | 6.19 | 0.73 | 11.8 |
| | 5.35 | | | |
| | 6.67 | | | |
| 0.50 | 2.74 | 3.92 | 2.48 | 63.2 |
| | 6.77 | | | |
| | 2.25 | | | |
| 1.00 | 5.44 | 7.52 | 1.91 | 25.35 |
| | 7.92 | | | |
| | 9.19 | | | |
| 2.00 | 8.97 | 6.22 | 3.22 | 51.8 |
| | 7.00 | | | |
| | 2.68 | | | |
| 4.00 | 5.48 | 4.00 | 1.52 | 38.1 |
| | 4.09 | | | |
| | 2.44 | | | |
| 8.00 | 1.79 | 2.23 | 0.40 | 18.0 |
| | 2.31 | | | |
| | 2.59 | | | |
| 24.0 | 0.00 | 0.00 | — | — |
| | 0.00 | | | |
| | 0.00 | | | |

TABLE 6

Pharmacokinetics parameters of CA77.1 after p.o. and i.v. administration in ICR (CD-1) mice

| | $T_{1/2}$ (h) | $T_{max}$ (h) | $C_{max}$ (ng/mL) | $AUC_{last}$ (h * ng/mL) | $AUC_{INF\_obs}$ (h * ng/mL) |
|---|---|---|---|---|---|
| p.o. | 2.78 | 1.0 | 464 | 1456 | 1460 |
| i.v. | 1.39 | — | — | 314 | 315 |

| | $CL_{obs}$ (mL/min/kg) | $MRT_{INF\_obs}$ (h) | $VSS_{obs}$ (mL/kg) | F % |
|---|---|---|---|---|
| p.o. | — | 3.0 | — | 46.4 |
| i.v. | 3177 | 2.0 | 6463 | |

Example 6. Metabolic Stability in Human, Rat, and Mouse Microsomes

Microsome stability was determined in human, rat, and mouse, liver microsomes. Compound at 3 μM final concentration along with 0.5 mg/mL microsome protein and 1 mM NADPH was incubated for 0, 5, 15, 30 and 60 min. As a negative control, test compound was incubated with microsomes in the absence of NADPH. Samples were quenched with methanol and centrifuged for 25 min at 2500 rpm to precipitate proteins. Supernatants were analyzed (N=3) by LC-MS/MS. The ln peak area ratio (compound peak area/internal standard peak area) was plotted against time and the gradient of the line determined the elimination rate constant [k=(−1)(slope)]. The half life ($t_{1/2}$ in minutes), incubation volume (V in μL/mg protein) and the in vitro intrinsic clearance ($CL_{int}$ in μL/min/mg protein) were calculated according to the following equations:

Half life $(t_{1/2})$(min)=0.693/k  (1)

$V$ (μL/mg)=volume of incubation (μL)/protein in the incubation (mg)  (2)

Intrinsic Clearance $(CL_{int})$ (μL/min/mg protein)=$V$*0.693/$t_{1/2}$  (3)

Tables 7 provides a comparison of the stability of CA77 and CA77.1 in human microsomes. Table 8 provides a comparison of the stability of CA39 and CA39.1 in human microsomes. Testosterone, diclofenac, and propafenone are provided as controls. $R^2$ is the correlation coefficient of the linear regression for the determination of kinetic constant. $T_{1/2}$ is the half life and $CL_{int\ (mic)}$ is the intrinsic clearance. $CL_{int(liver)}=CL_{int\ (mic)}$*mg microsomal protein/g liver weight*g liver weight/kg body weight. Liver weight/kg body weight is 20 g/kg for human.

TABLE 7

Metabolic Stability of CA77 and CA77.1 in Human Microsomes

| Sample | $R^2$ | $T_{1/2}$(min) | $CL_{int(mic)}$ (μL/ min/kg) | $CL_{int(liver)}$ (mL/ min/kg) | Remaining (T = 60 min) |
|---|---|---|---|---|---|
| CA77.1 | 0.9301 | 20.6 | 67.2 | 60.5 | 10.8% |
| CA77 | 0.9493 | 34.0 | 40.8 | 36.7 | 25.9% |
| Testosterone | 0.9904 | 57.5 | 57.5 | 51.8 | 16.7% |
| Diclofenac | 0.9875 | 104.9 | 104.9 | 94.4 | 4.0% |
| Propafenone | 0.9692 | 159.1 | 159.1 | 143.2 | 0.8% |

TABLE 8

Metabolic Stability of CA39 and CA39.1 in Human Microsomes

| Sample | $R^2$ | $T_{1/2}$(min) | $CL_{int(mic)}$ (μL/ min/kg) | $CL_{int(liver)}$ (mL/ min/kg) | Remaining (T = 60 min) |
|---|---|---|---|---|---|
| CA39.1 | 0.1321 | >145 | <9.6 | <8.6 | 96.0% |
| CA39 | 0.9363 | 37.9 | 36.6 | 32.9 | 30.1% |
| Testosterone | 0.9983 | 13.5 | 102.8 | 92.5 | 4.6% |
| Diclofenac | 0.9973 | 15.7 | 88.0 | 79.2 | 6.8% |
| Propafenone | 0.9464 | 6.6 | 211.2 | 190.1 | 0.2% |

What is claimed is:
1. A compound of the Formula I

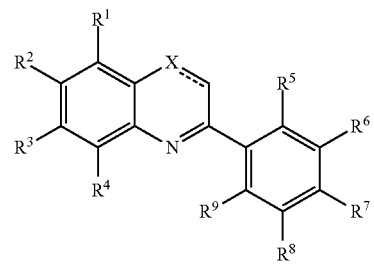

(I)

or a pharmaceutically acceptable salt thereof, wherein
X is O and ===== is a single bond, or X is N and ===== is a double-aromatic bond;
$R^1$, $R^3$, and $R^4$ are independently chosen from hydrogen, halogen, hydroxyl, $C_1$-$C_6$alkyl, and $C_1$-$C_6$alkoxy;
$R^2$ is halogen;
$R^5$, $R^6$, $R^8$, and $R^9$ are independently chosen from hydrogen, halogen, hydroxyl, $C_1$-$C_6$alkyl, and $C_1$-$C_6$alkoxy;
$R^7$ is phenyl, naphthyl, and mono- or bi-cyclic heteroaryl, each of which is substituted with one substituent chosen from —$NR^{10}COR^{11}$ and $NR^{10}SO_2R^{11}$, and wherein each of the phenyl, naphthyl, and mono- or bi-cyclic heteroaryl is optionally substituted with halogen, hydroxyl, cyano, —CHO, —COOH, amino, and $C_1$-$C_6$alkyl in which any carbon-carbon single bond is optionally replaced by a carbon-carbon double or triple bond, any methylene group is optionally replaced by O, S, or NR$^{12}$, and optionally substituted with one or more substituents independently chosen from halogen, hydroxyl, cyano, amino, and oxo; and R$^{10}$ is independently chosen at each occurrence from hydrogen and C$_1$-C$_6$alkyl;

R$^{11}$ is independently chosen at each occurrence from hydrogen, C$_1$-C$_6$alkyl, C$_1$-C$_2$haloalkyl, monocyclic aryl and heteroaryl, each of which monocyclic aryl and heteroaryl is optionally substituted with one or more substituents independently chosen from halogen, hydroxyl, cyano, C$_1$-C$_6$alkyl, C$_1$-C$_6$alkoxy, C$_1$-C$_2$haloalkyl, and C$_1$-C$_2$haloalkoxy; and R$^{12}$ is hydrogen, C$_1$-C$_6$alkyl, or (C$_3$-C$_7$cycloalkyl)C$_0$-C$_2$alkyl.

2. A compound or salt of claim 1, where X is O and ===== is a single bond.

3. A compound or salt of claim 1, where X is N and ===== is a aromatic bond.

4. A compound or salt of claim 1, wherein R$^1$, R$^3$, and R$^4$ are all hydrogen.

5. A compound or salt of claim 1, wherein R$^2$ is chloro.

6. A compound or salt of claim 1, wherein R$^5$, R$^6$, R$^8$, and R$^9$ are all hydrogen.

7. A compound or salt of claim 1, wherein

R$^7$ is phenyl, napthyl, pyrrolyl, pyrazolyl, thienyl, furanyl, imidazolyl, thiazolyl, triazolyl, pyridyl, pyrmidinyl, benzimidazolyl, imidazopyridizinyl, indolyl, indazolyl, quinolinyl, or isoquinolinyl, each of which is optionally substituted with one or more substituents independently chosen from halogen, hydroxyl, cyano, —CHO, COOH, amino, and C$_1$-C$_6$alkyl in which any carbon-carbon single bond is optionally replaced by a carbon-carbon double or triple bond, any methylene group is optionally replaced by O, S, or NR$^2$, and optionally substituted with one or more substituents independently chosen from halogen, hydroxyl, cyano, amino, and oxo; and substituted with one substituent chosen from —NR$^{10}$COR$^{11}$ and NR$^{10}$SO$_2$R$^{11}$;

R$^{10}$ is independently chosen at each occurrence from hydrogen and C$_1$-C$_6$alkyl; and R$^{11}$ is independently chosen at each occurrence from C$_1$-C$_2$haloalkyl, C$_3$-C$_7$cycloalkyl, monocyclic aryl and heteroaryl, each of which monocyclic aryl and heteroaryl is optionally substituted with one or more substituents independently chosen from halogen, hydroxyl, cyano, C$_1$-C$_6$alkyl, C$_1$-C$_6$alkoxy, C$_1$-C$_2$haloalkyl, and C$_1$-C$_2$ haloalkoxy; and R$^{12}$ is hydrogen, C$_1$-C$_6$alkyl, or C$_3$-C$_7$cycloalkyl.

8. A compound or salt of claim 1, wherein

R$^{11}$ is independently chosen at each occurrence from C$_1$-C$_2$haloalkyl, phenyl and pyridyl, each of which phenyl and pyridyl is optionally substituted with one or more substituents independently chosen from halogen, hydroxyl, cyano, C$_1$-C$_6$alkyl, C$_1$-C$_6$alkoxy, C$_1$-C$_2$haloalkyl, and C$_1$-C$_2$haloalkoxy.

9. A compound or salt of claim 1, where

R$^7$ is phenyl, optionally substituted with one or more substituents independently chosen from halogen, hydroxyl, C$_1$-C$_4$alkyl, C$_1$-C$_4$alkoxy, trifluoromethyl, and trifluormethoxy; and substituted with one substituent chosen from —NR$^{10}$COR$^{11}$ and NR$^{10}$SO$_2$R$^{11}$.

10. A compound or salt of claim 1, where

X is O and ===== is a single bond;

R$^1$, R$^3$, R$^4$, R$^5$, R$^6$, R$^8$, and R$^9$ are hydrogen;

R$^2$ is chloro; and

R$^7$ is phenyl, optionally substituted with one or more substituents independently chosen from hydroxyl and C$_1$-C$_2$alkoxy, and substituted with one substituent chosen from —NR$^{10}$COR$^{11}$ and NR$^{10}$SO$_2$R$^{11}$.

11. A compound or salt of claim 1, where

X is N and ===== is a aromatic bond;

R$^1$, R$^3$, R$^4$, R$^5$, R$^6$, R$^8$, and R$^9$ are hydrogen;

R$^2$ is chloro;

R$^7$ is phenyl, optionally substituted with halogen, and substituted with —NR$^{10}$COR$^{11}$, or NR$^{10}$SO$_2$R$^{11}$;

R$^{10}$ is hydrogen; and

R$^{11}$ is chosen from C$_1$-C$_2$haloalkyl, and phenyl, each of which phenyl optionally substituted with one or more halogens.

12. A compound or salt thereof of claim 1, wherein the compound is selected from

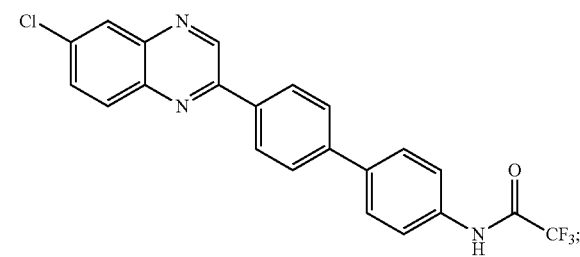

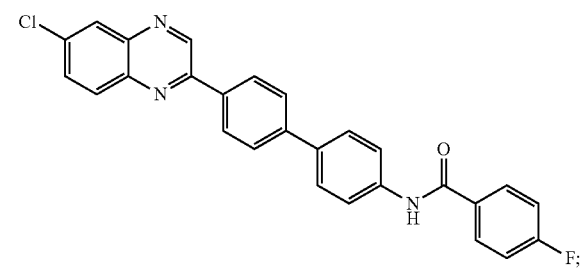

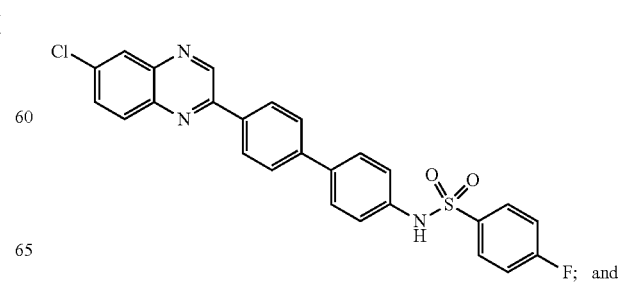

-continued

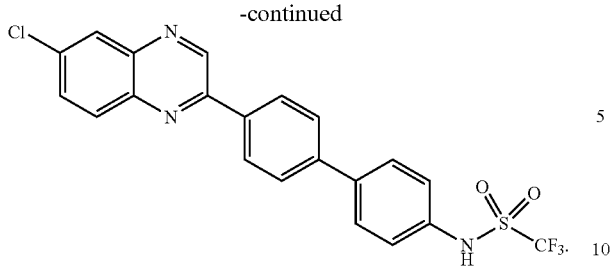

13. A pharmaceutical composition comprising a compound or salt of claim 1, together with a pharmaceutically acceptable carrier.

14. A method of selectively activating chaperone-mediated autophagy in a subject in need thereof, comprising administering an effective amount of a compound of claim 1 to the subject.

15. The method of claim 14, wherein the subject has Parkinson's disease, Huntington's disease, Alzheimer's disease, frontotemporal dementia, prion diseases, amyotrophic lateral sclerosis, retinal degeneration, Leber congenital amaurosis, diabetes, acute liver failure, NASH, hepatosteatosis, alcoholic fatty liver, renal failure and chronic kidney disease, emphysema, sporadic inclusion body myositis, spinal cord injury, traumatic brain injury, a lysosomal storage disorder, a cardiovascular disease, or immunosenescence.

16. A pharmaceutical composition comprising a compound or salt thereof, together with a pharmaceutically acceptable carrier, wherein the compound is

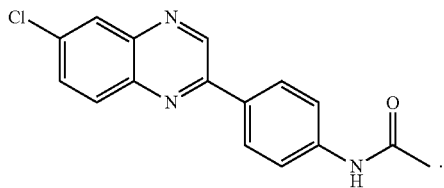 [SMILES: CC(=O)Nc1ccc(-c2cnc3cc(Cl)ccc3n2)cc1]

17. A pharmaceutical composition comprising a compound or salt thereof, together with a pharmaceutically acceptable carrier, wherein the compound is

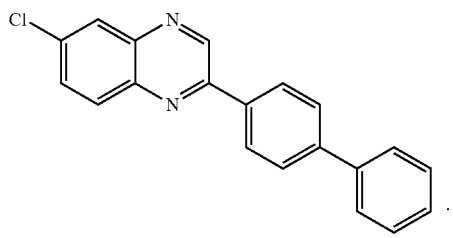 [SMILES: Clc1ccc2nc(-c3ccc(-c4ccccc4)cc3)cnc2c1]

18. A method of selectively activating chaperone-mediated autophagy in a subject in need thereof, comprising administering an effective amount of a pharmaceutical composition of claim 16 to the subject, wherein the subject has Parkinson's disease, Huntington's disease, Alzheimer's disease, frontotemporal dementia, prion diseases, amyotrophic lateral sclerosis, retinal degeneration, Leber congenital amaurosis, diabetes, acute liver failure, NASH, hepatosteatosis, alcoholic fatty liver, renal failure and chronic kidney disease, emphysema, sporadic inclusion body myositis, spinal cord injury, traumatic brain injury, a lysosomal storage disorder, a cardiovascular disease, or immunosenescence.

19. A method of selectively activating chaperone-mediated autophagy in a subject in need thereof, comprising administering an effective amount of a pharmaceutical composition of claim 17 the subject, wherein the subject has Parkinson's disease, Huntington's disease, Alzheimer's disease, frontotemporal dementia, prion diseases, amyotrophic lateral sclerosis, retinal degeneration, Leber congenital amaurosis, diabetes, acute liver failure, NASH, hepatosteatosis, alcoholic fatty liver, renal failure and chronic kidney disease, emphysema, sporadic inclusion body myositis, spinal cord injury, traumatic brain injury, a lysosomal storage disorder, a cardiovascular disease, or immunosenescence.

* * * * *